United States Patent
Cover et al.

(10) Patent No.: US 8,180,148 B2
(45) Date of Patent: May 15, 2012

(54) IMAGING APPARATUS AND METHOD OF FORMING COMPOSITE IMAGE FROM A PLURALITY OF SOURCE IMAGES

(75) Inventors: Keith S. Cover, Amsterdam (NL); Frank J. Lagerwaard, Amsterdam (NL); Suresh Senan, Amsterdam (NL)

(73) Assignee: VU Medisch Centrum, Amsterdam (NL)

( * ) Notice: Subject to any disclaimer, the term of this patent is extended or adjusted under 35 U.S.C. 154(b) by 893 days.

(21) Appl. No.: 11/814,665

(22) PCT Filed: Jan. 24, 2006

(86) PCT No.: PCT/NL2006/000035
§ 371 (c)(1),
(2), (4) Date: Apr. 9, 2008

(87) PCT Pub. No.: WO2006/080836
PCT Pub. Date: Aug. 3, 2006

(65) Prior Publication Data
US 2008/0317305 A1    Dec. 25, 2008

Related U.S. Application Data

(60) Provisional application No. 60/647,099, filed on Jan. 26, 2005, provisional application No. 60/695,945, filed on Jun. 30, 2005.

(51) Int. Cl.
*G06K 9/00* (2006.01)
(52) U.S. Cl. ....................................................... 382/162
(58) Field of Classification Search .................. 382/100, 382/112, 128, 135, 136, 141, 144, 145, 165, 382/206; 348/86, 87, 92, 93; 356/73, 237.1, 356/237.2; 250/559.39–559.45
See application file for complete search history.

(56) References Cited

U.S. PATENT DOCUMENTS

| | | | |
|---|---|---|---|
| 5,216,602 A | 6/1993 | Wolfkiel et al. |
| 5,970,167 A | 10/1999 | Colvin |
| 6,535,570 B2 | 3/2003 | Stergiopoulos et al. |
| 6,690,965 B1 | 2/2004 | Riaziat et al. |

(Continued)

FOREIGN PATENT DOCUMENTS

EP    1 107 012 A1    6/2001
(Continued)

OTHER PUBLICATIONS

Diez et al., "Analysis and evaluation of periodic physiological organ motion in radiotherapy treatments." *Radiotherapy and Oncology* 73(2004): 325-329.

(Continued)

*Primary Examiner* — Jose Couso
(74) *Attorney, Agent, or Firm* — Merchant & Gould P.C.

(57) ABSTRACT

Source images, in particular images used for the planning radiotherapy, using internal images of the human body obtained with techniques such as X ray techniques, are processed to form a colored composite image that depends in a robust way on differences between different ones of the source images. For each pixel position in the composite image, the maximum image value in the different source images is determined and used to control brightness of the composite image. For each pixel position, an amount of spread in the images values among the source images is determined and used to control a color saturation in the composite image.

30 Claims, 2 Drawing Sheets

U.S. PATENT DOCUMENTS 6,801,651 B2 * 10/2004 Yonezawa ............... 382/145
6,804,384 B2 10/2004 Lowen

FOREIGN PATENT DOCUMENTS

| | | |
|---|---|---|
| EP | 1 420 367 A1 | 5/2004 |
| EP | 1 846 890 A0 | 10/2007 |
| WO | WO 97/26507 | 7/1997 |
| WO | WO 2006/080836 A2 | 8/2006 |

OTHER PUBLICATIONS

Taxt et al., "Advances in Medical Imaging." *Pattern Recognition* 1998(1: 16): 505-508. XP010297652.

Kato et al., "Prediction of impending ruptutre in aneurysms using 4D-CTA: Histopathological verification of a real-time minimally invasive tool in unruptured aneurysms." *Minim. Invas. Neurosurg.* 2004(47): 131-135.

Romer et al., "Positrion emission tomography in Non-Hodgkins Lymphoma: Assessment of chemotherapy with fluourodeoxyglucose." *Blood* 91: 12(1998): 4464-4471.

Arnold et al., The Java Programming Language ($3^{rd}$ Edition). Addison Wesley, Boston, 2000.

Bhargava et al., "High resolution parametric imaging for the assessment of organ blood perfusion and its dynamics," *Proceedings of the Computers in Cardiology Meeting, Chicacgo* (Sep. 1990) 129-132. XP010024758.

Cover et al., "Color intensity projection of digitally subtracted angiography for the visualization of brain arteriovenous malformations," *Neurosurgery* (2007) 60 (3): 511-515. XP009112333.

Cover et al., "Color intensity projections: A rapid approach for evaluating four-dimensional CT scans in treatment planning," *International Journal of Radiation: Oncology Biology Physics* (2006) 64 (3): 954-961. XP024897762.

Hunter et al., "Parametric imaging using digital subtraction angiography," *The British Journal of Radiology* (1986) 59: 7-11. XP009149179.

Rheingans et al., "Perceptual principles for effective visualizations," *Perceptual Issues in Visualization* (1995): 59-74. XP002515604.

Search Report for related European App. No. EP 11164498.5 mailed on Jun. 21, 2011.

* cited by examiner

IMAGING APPARATUS AND METHOD OF FORMING COMPOSITE IMAGE FROM A PLURALITY OF SOURCE IMAGES

FIELD OF THE INVENTION

The invention relates to a method of forming an image of an object and to an apparatus for forming such an image. In one particular aspect the invention relates to forming a single image that represents a temporal series of images of a patient for the purpose of planning radiotherapy.

BACKGROUND ART

From U.S. Pat. No. 6,690,965 it is known to plan locations for the application of radiotherapy to a patient. It is desirable that during radiation therapy the radiation dose should be applied to tumors and not to healthy tissue. Accordingly, radiotherapists typically plan a "window" where radiotherapeutic radiation is applied dependent on the location of the relevant tissue. In order to form the plan, the radiotherapist typically analyzes images of a patient, such as X-ray CT (Computer Tomography) images to locate relevant tissue. Use may be made of so-called 4D-CT X-ray images, that are resolved both in three dimensions in space and in time (see for example U.S. Pat. No. 6,535,570), but alternatively other techniques may be used to obtain the images, such as NMR imaging, fluoroscopy, acoustical echography etc.

Tissue moves due physiological cycles such as the respiratory cycle and the cardiac cycle. In practice radiotherapists often ignore this movement during planning by analyzing only one image that has been obtained for a specific time point or integrated over a larger time interval. To take account of tissue movement, radiotherapists typically would have to analyze a series of images of a patient in order to plan where radiation needs to be applied and when the radiation needs to be applied during the physiological cycle. This considerably complicates planning.

The use of false color images for planning radiotherapy has been proposed in an article titled "Analysis and evaluation of periodic physiological organ motion in radiotherapy treatments", by Sergio Díez, Javier García and Francisco Sendra, and published in Radiotherapy and Oncology 73 (2004) pages 325-329. This article proposes to identify a respiratory cycle and to select images of a patient at maximal exhalation and maximal inhalation during this cycle. Furthermore the article proposes to compute what it calls a probability density function (PDF) which is an average of the images of the patient during the cycle.

The article proposes forming of a composite color image, wherein the red component of a pixel is controlled by the corresponding pixel of image at maximal inhalation, the green component is controlled by the corresponding pixel of the image at maximal exhalation and the blue component is controlled by the corresponding pixel of the PDF. As a result a pixel of the composite image will be grey if the corresponding pixels in the source images are all equal. In this case the pixel assumes the value that the pixel has in all the source images. However, certain changes during the cycle will show up as color in the composite image, particularly when a pixel has different values at maximum inhalation and maximum exhalation or when the average value differs from these values. The article notes that the resulting composite image is useful for motion detection, since the human observer is more sensitive to changes in color than in grey levels.

This technique has the disadvantage that it is dependent on the selection of images at maximum inhalation and exhalation. The technique is not robust against errors in the selection of these images. Differences between these images have a strong effect on the overall appearance of the composite image. Moreover, if a pixel is the same in these two images, but changes in between it shows up with completely different color compared to pixels that are different in the images of maximum inhalation and exhalation. This makes it difficult to use the composite image for planning of radiotherapy.

An alternative current solution for showing a series of images is to show these images successively as a "motion picture" that is repeated indefinitely. However, typically this does not enable the radiotherapist to plan the radiation treatment. Therefore current practice, if the analysis is not limited to a single image, is to analyze the images one by one, at the expense of a prolonged time for analysis.

Another technique for forming images for inspection by radiotherapists is "maximum intensity projection". According to this technique the X-ray absorption profile is measured from a series of two dimensional slices of the body and the measurements are combined into a single composite image using, for each pixel, the maximum intensity (maximum absorption) at a corresponding position any of the different slices. This technique has the effect that any bones will show up clearly: bones have high absorption and if there is high absorption at a position in any of the slices this will control the composite image intensity. However, this technique by itself is not useful for planning radiotherapy, because the maximum intensity does not show whether movement occurs.

From U.S. Pat. No. 6,804,384 an NMI (Nuclear Magnetic resonance Imaging) system is known wherein color is used for joint encoding of a magnetic resonance property and a function of that property in order to enhance display of certain image regions on the basis of hue brightness and saturation. Various examples of functions are given, such as the presence of material in the corresponding region or homogeneity of material in the corresponding region.

U.S. Pat. No. 6,690,965 describes the detection of movement by subtraction of images that have been obtained at different time points. Moreover it is known from acoustic echography to detect flow speeds by means of measurements of Doppler shift and to composite images that show the detected flow speeds.

All these techniques offer the possibility to generate images that can, in theory, be interpreted more quickly by a physician. Usually considerable experience is needed to interpret this kind of images properly. Typically, physicians have highly developed skills for interpreting conventional source images such as X-ray CT images, but these skills are only of limited use for planning radiotherapy, for example, from images wherein pixel data encodes movement.

SUMMARY OF THE INVENTION

Among others, it is an object of the invention to provide a method and system for generating a composite color image wherein color is used to represent image differences in a series of source images, preferably internal images of the human body obtained with techniques such as X ray techniques, in such a way that the degree to which color is present is robust against variations in the way that the source images are selected.

Among others, it is a further object of the invention to provide such a method and system so that the degree to which color is present in the resulting composite image does not depend on selection of specific images.

Among others, it is a further object of the invention to provide such a method and system so that the way in which difference between the source images affect color is the same irrespective of the position of the source image wherein the change occurs during a physiological cycle.

Among others, it is an object of the invention to process source images, preferably internal images of the human body obtained with techniques such as X ray techniques, in a way that makes it possible to use the information containing capacity of a colored composite image efficiently in such a way that the generated composite image corresponds to the source images when the source images are substantially identical and that information about differences between the source images is represented with a minimum of disturbance of the information about the shared properties of the source images.

Among others, it is an object of the invention to provide for a method of generating image from measured data for a series of source images, so that the generated image is controlled both by static and dynamic spatial properties of the measured data in such a way that the generated image corresponds to the source images when the source images are substantially identical.

Among others, it is an object of the invention to provide for a method of generating a colored composite image from measured data for a series of source images, so that the encoding capacity of the composite image is used to encode both by static and dynamic properties of the measured data in such a way that the timing at which the source images are obtained and their number does not significantly affect the resulting composite image.

A method of forming an image according to the invention is set forth in claim 1. According to the invention color saturation at each pixel position of the generated composite image is controlled by a spread between maximal and minimal intensity of pixel values at the corresponding pixel positions in a series of source images.

In a further embodiment, brightness is controlled by an extreme of the pixel values at the corresponding pixel positions in a series of source images. For example in medical imaging said selecting of the extreme value preferably involves selecting an image value that is indicative of a highest likelihood of a predetermined type of tissue at the particular pixel position in any one of the source images, e.g. highest absorption in an X-ray image. In this way the generated image basically looks like any of the source images, so that persons skilled at interpreting such source images can use his or her basic skills for interpreting the generated image. The effect of the maximum differences between all the source images is made visible by means of deviations in color, without significantly impairing interpretation the original.

It may be noted that the maximum and minimum pixel values generally do not correspond to the pixel values in the images of maximum exhalation and inhalation. Some of the maximum values for individual pixels may come from the image for maximum inhalation, while maximum values for other pixels come from the image for minimum inhalation, and still others may come from other images. Therefore a much more consistent representation is realized than is possible when the image is controlled by the images at minimum and maximum inhalation. Moreover, by using spread at individual pixel positions to control saturation and optionally extreme values at individual pixel positions to control brightness, the noise in the resulting composite image is reduced in comparison with the technique where only the two images at minimum and maximum inhalation are used.

In another embodiment, pixel value windowing is applied prior to the determination of the spread. This makes it possible to generate a composite image directed at a selected type of tissue. Preferably, the pixel value window is user-interactively selectable.

In another embodiment the hue of the pixel values in the composite color image is selected under control of a central value corresponding to pixel values in the source images, such as for example an average value or a median, or a value that has a predetermined rank in a list of the image values of the source image according to intensity, wherein the predetermined rank is between, say, four tenths and six tenth of the number of image values. In this way more information that is relevant to radiotherapy is included in the composite image, while still remaining compatible with conventional images. Preferably, in this embodiment, pixel value windowing is applied prior to the determination of the central value. This makes it possible to generate a composite image directed at a selected type of tissue. Preferably, the pixel value window is user-interactively selectable.

BRIEF DESCRIPTION OF THE DRAWING

These and other objects and advantageous aspects of the invention will be described by means of non-limitative examples shown in the following figures.

DETAILED DESCRIPTION OF THE EMBODIMENTS

Figure 1:
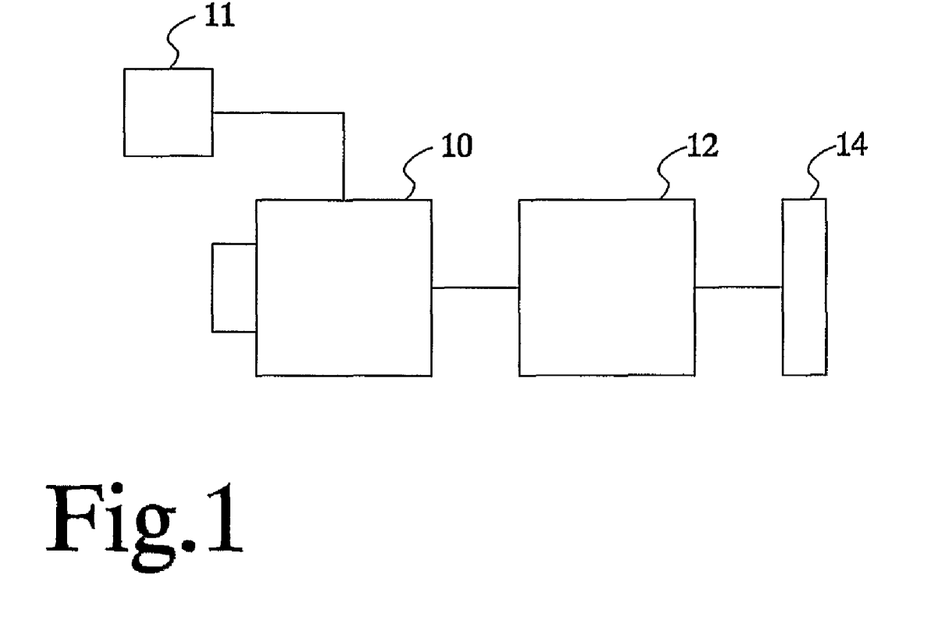
FIG. 1 shows an image acquisition system

FIG. 1 shows an image acquisition system, comprising a computer tomography device 10, a physiological cycle detector 11, an image processing computer 12 and an image display device 14. Image processing computer 12 has an input coupled to couple to computer tomography device 10 and an output coupled to image display device 14. Physiological cycle detector 11 is coupled to computer tomography device 10.

In operation computer tomography device 10 is operated to obtain a series of temporally successive images of internal organs a patient, for example at respective phase points spread over a respiratory cycle, or any other physiological cycle, such as the cardiac cycle. Conventional image acquisition techniques may be used to acquire the images for the selected time points, or for providing images from which images for the selected time points may be selected.

Although a computer tomography device 10 is preferred, it should be understood that other image acquisition techniques may be used, such as fluoroscopy, NMR or acoustical echography. Preferably detector 11 is used to detect the cycle and signals the series of time points at which images should be obtained, for example ten time points spread substantially equidistantly over the full period of the cycle, or (optionally repeated) groups of time points around a predetermined phase point in one or more successive cycles. Use of points distributed with sufficient density over an entire cycle has the advantage that all movement will be detected. Use of groups of time points near a predetermined phase in one or more successive cycles may be used if irradiation for radiotherapy is contemplated near that phase point and high resolution insight about motion is required. However, it should be appreciated that other techniques may be used. For example, a detection of the cycle may be obtained from the images themselves or by the operator of the apparatus. In any case it is not essential that the observations are limited to a single physiological cycle at long at images spread over at least a full cycle are obtained.

Also it should be appreciated that in other applications cycle related selection of images may not be necessary, for example if the source images are acquired of an organ during successive visits of a patient to a physician over a longer period of say, months.

After acquisition computer tomography device sends information about the content of each of the temporally successive images to image processing computer 12. Image processing computer 12 combines information from the temporally successive image into a single composite image and controls image display device 14 to display the composite image. It should be appreciated that image processing computer 12 may also perform other image processing tasks, for example tasks for determining slice images from raw data for tomography purposes.

Figure 2:
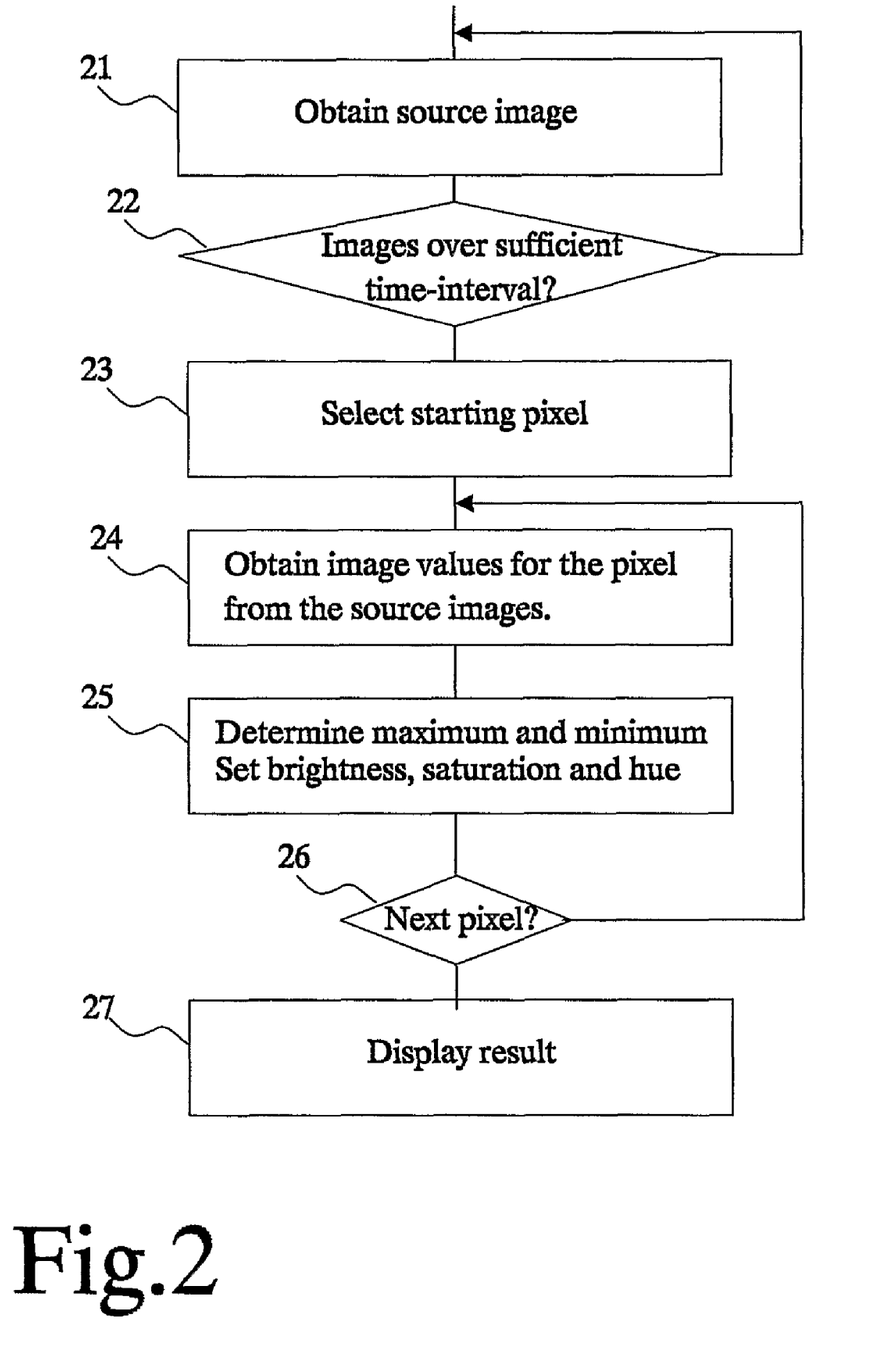
FIG. 2 shows a flow chart of an image generation process

FIG. 2 shows a flow-chart of the image forming process. In a first step 21a source image of a patient is obtained with computer tomography device 10. An image, as used herein, is a set of data values for measurement positions that are spatially distributed over an at least two-dimensional spatial region. In a second step 22 it is determined whether source images have been obtained spread over a full physiological cycle. If not the process is repeated from first step 21, for acquiring further images, for example ten images during the physiological cycle, but other numbers of images may be used. Also, images may be obtained over more than a physiological cycle.

Once images have been obtained spread at least over the full physiological cycle the process proceeds to a third step 23 wherein image processing computer 12 selects a first pixel position in the composite image. Later on, in a sixth step 26 the process will be repeated until all pixel locations in the composite image have been treated. It should be noted that "image" in respect of this repetition refers to any set of two-dimensionally arranged pixel values. Without deviating from the invention the image for which sixth step 26 causes the preceding steps to be repeated can be part of a larger image of which the remaining pixels may be treated differently.

It should be appreciated that the flow-chart is used merely to illustrate an example of such a process: it is not necessary that all actions are performed exactly in the order shown in the flow chart. For example, in the flow chart successive source images are obtained before performing other steps on a pixel by pixel basis, but it will be appreciated that alternatively at least part of the pixel by pixel steps may be performed using part of the obtained images before obtaining further images.

After third step 23, in a fourth step 24, image processing computer 12 obtains image values for the selected pixel position from the series of source images. Typically, each source image contains the same array of pixels, in which identical pixel positions may be used. However, in an embodiment the source images are registered first, that is, offset values between corresponding pixel positions for different source images are determined so that these pixel positions have the same relative position with respect to a reference coordinate frame.

In a fifth step 25 image processing computer 12 selects a color pixel value for the pixel position in the composite image. Image processing computer 12 selects brightness, hue and color saturation of this pixel value. Together these three properties control the pixel value.

In fifth step 25 image processing computer 12 determines the maximum and minimum values among the image values from the source images at the corresponding positions. The image processing computer 12 uses the resulting maximum to control the brightness of a color pixel value at the pixel position in the composite image. When the image values in the source images represent values on the same brightness scale as the result image the brightness in the composite image preferably equals the maximum. Otherwise, brightness in the composite image may be set equal to the maximum possible value in the composite image times the maximum value found for the pixel in source images divided by the maximum possible value in source image. An example of a mathematical formula that may be applied for this purpose is $$\text{brightness} = \max$$

(here both brightness and the maximum "max" are assumed to be normalized on a scale from zero to one for minimum possible and maximum possible brightness respectively). Although a specific mathematical formula is given here, it should be appreciated that, without deviating from the invention, a different control of brightness may be used. For example in another embodiment only part of the brightness scale may be used, or the brightness may be a non-linear, but generally increasing function of "max".

In an embodiment image processing computer 12 selects a predetermined hue for the color pixel value at the pixel position in fifth step 25. However, as will be discussed later, hue is preferably also selected dependent on the source images.

Also in fifth step 25 image processing computer 12 controls color saturation in proportion to the difference between the maximum and minimum image values that have been found for the pixel position. Typically the saturation value is set equal to the maximum allowable saturation value time the difference between the maximum and the minimum, divided by the maximum. Thus, saturation is proportional to the spread in image values at the pixel location. But, without deviating from the invention the saturation may be another generally increasing function of the difference between the minimum and maximum. An example of a mathematical formula that may be applied for this purpose is $$\text{Saturation} = (\max - \min)/\max$$

("min" denotes the minimum and a saturation is used that is normalized on a scale from zero to one). Although a specific mathematical formula is given here, it should be appreciated that, without deviating from the invention, a different control of saturation may be used. For example in another embodiment only part of the saturation scale may be used, preferably starting from zero saturation when max=min, or saturation may be a non-linear, but generally increasing function of "max-min".

Figure 3:
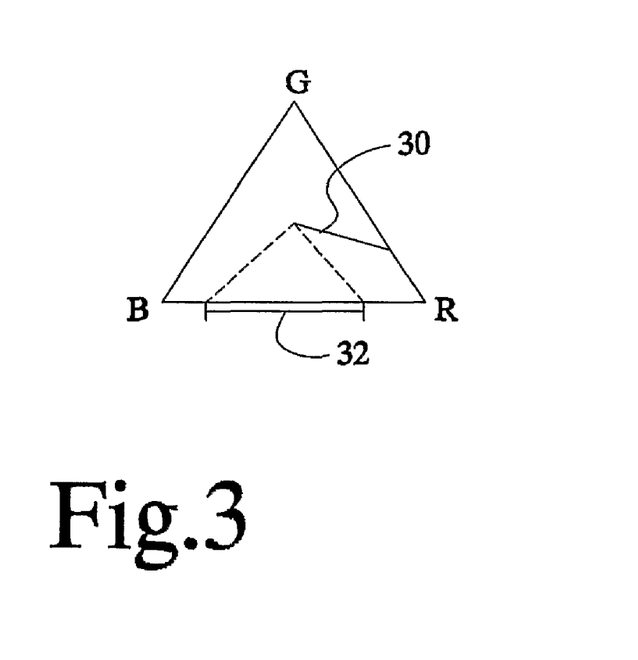
FIG. 3 shows a color triangle

FIG. 3 schematically shows a color triangle. A color triangle forms a conventional representation of hue and saturation. In the schematic representation of FIG. 3 the corners of the triangle represent pure red, green and blue and the centre of the triangle represents white. The color and hue values selected in fifth step 25 lie along a line 30 of points in the triangle that represent the same hue and increasing saturation, starting at the centre of the triangle (zero saturation) and ending at a side of the triangle or a corner (maximum saturation). Of course, the color triangle is merely an illustration of this effect; equivalent different representations, such as known color circles could be used, wherein line 30 would be a radius.

After fifth step 25 image processing computer 12 executes a sixth step, wherein an new pixel location is selected to which fourth step 24 and fifth step 25 will be applied. This is repeated until all pixel positions in the composite image have been treated. Subsequently image processing computer 12 executes a seventh step 27, wherein it causes image display device 14 to display the composite image with the color pixel values that have been computed in the preceding steps. In one embodiment a display device 14 may be used that is controlled directly by brightness, hue and saturation signals. In other embodiments a display device 14 may be used that requires other control signals, such as RG and B values. In this case, any known conversion technique may be used to convert the selected brightness, hue and saturation into the appropriate control signals for display device 14, or the appropriate control signals may be computed directly in fifth step 25, using vector arithmetic to compose RGB vectors for example. An example of such a conversion is described in Arnold, K., Gosling, J. & Holmes, D. The Java programming language 3rd Ed. (Addison Wesley, Boston, 2000). As will be appreciated the resulting image is a grey-scale image at those pixel locations for which no significant differences occur between the images values in the source images. Color display occurs at locations where significant differences occur between these images values. It has been found that this aids radiotherapists to plan radiotherapy using mainly the single composite image for the entire physiological cycle. It should be appreciated that this does not depend on what is specifically displayed, but on how the information is used to compact information in the composite image so that it will have the desired ergonomic effect. As can be appreciated the resulting composite image does not depend on the number of images that has been acquired during the physiological cycle, provided that the time points at which the images are acquired are not so sparse that no overlap occurs of images of local regions with similar measured properties.

In a further embodiment image processing computer 12 in fifth step 25 also selects hue dependent on the source images. In this further embodiment image processing computer 12 computes the mean of the image values of the source images for the pixel position that is being treated and selects a hue value from a predetermined hue scale dependent on the value of the mean. Typically the hue scale contains successive hues from a predetermined segment 32 of the color triangle, e.g. from red to green, the position of the selected hue in segment 32 being determined by the mean divided by the maximum. The saturation with which this hue is rendered is determined as described before. It has been found that this aids radiotherapists even further to plan radiotherapy using mainly the single composite image for the entire physiological cycle. An example of a mathematical formula that may be applied for this purpose is $$Hue=\tfrac{2}{3}*(mean-min)/(max-min)$$

(herein hue is normalized on a scale from zero to one, where zero corresponds to red, $\tfrac{2}{3}$ corresponds to blue and green corresponds to an intermediate value between zero and $\tfrac{2}{3}$. Of course other scales may be used for hue, whether they be widely excepted standards, custom designed, or selected in some other manner.).

Although the use of the mean has been described for controlling hue in this embodiment, it should be realized that a similar effect can be realized with other central values, like the median of the image values or a value at a predetermined rank according to the size of the image values. Also, of course the hue can be controlled by a function of such a central value, such as the square of the value for example.

In an alternative embodiment hue is controlled in a by information that is indicative of a time point where an object first appears at a pixel location. In the embodiment wherein images are obtained for time points distributed over a physiological cycle of the patient, information is used that is indicative of a phase point in that cycle where the object first appears at the pixel location.

In one version of this alternative embodiment for each pixel and for each of a series of time or phase point the maximum image value of the pixel up to the time point from a start of measurement is determined. These cumulative maxima are averaged over time. Preferably the starting point for the determination and for the averaging time interval is determined by some external event, such as the injection of a contrast fluid into the patient. The average is used to control hue at the pixel location, for example according to $$Hue=\tfrac{2}{3}*(average\ cumulative\ maximum)/max$$

Thus, dynamical changes in the image are converted into static data, which can be more conveniently inspected. When use is made of a detected physiological cycle the maximum image value of the pixel in an interval from a starting phase point up to the phase point in the physiological cycle is determined and this cumulative maximum is averaged over the cycle.

It should be appreciated that alternative methods are possible for determining the time point of appearance. For example an edge detection method may be used to detect a time point where the image value of the pixel as a function of time exhibits an edge. However, use of the average of the cumulative maximum provides results that are more robust against noise. Instead of a maximum in a time interval from the start of a measurement period (or physiological cycle) to the time point, a minimum of the image value from the time point to an end of a measurement period (or physiological cycle) may be used. Either of these are preferably used when an event is created that increases the image value as a function of time (e.g. when absorptive contrast fluid is injected into a patient and increased absorption results in an increased image value). Of course the role of maximum and minimum may be reversed, for example if the event leads to a decreased image value as a function of time. As a further alternative both images obtained using a cumulative maximum and an image obtained using a cumulative minimum may be computed and shown (i.e. images wherein the roles of maximum and minimum in determining the time point of appearance are mutually reversed), or a combination of such images may be produced.

In another further embodiment a "pixel-value windowing" step precedes fifth step 25. Pixel-value windowing is known per se for the purpose of processing an image prior to display, in order to analyse selected types of tissue. In general, pixel value windowing involves clamping pixel values outside a selected range. That is, pixel values that are below the range are replaced by the lower bound of the range and pixel values that are above the range are replaced by the upper bound of the range. This may be applied to grey pixel values or RGB pixel values. Conventionally this technique is used prior to display of a grey scale image, whereby serves to show detail of a selected type of tissue, while suppressing details of unselected tissue.

In the present further embodiment, however, pixel-value windowing is applied prior to processing according to fifth step 25, that is, not merely to affect display, but also to affect how changes in the image content will be converted to a composite image. For example, applied before the computation of the saturation, pixel value windowing can be used to suppress color in the composite image (keep saturation at zero) at pixel locations where the maximum and the minimum input value are either both below a lower bound or both above an upper bound. This can be used to suppress uninteresting detail, such as details of bone structure or details in regions where only air is present. Furthermore application of pixel value windowing before the computation of saturation can be used to ensure that the saturation is not affected by fluctuations in a range of small input values (lowest X-ray absorption), or to ensure that the saturation is not affected by fluctuations of big input values (high X-ray absorption).

Similarly, applied before the computation of hue as a function of the central tendency, pixel value windowing can be used to suppress changes in hue due to the temporary presence of selected types of tissue at a location that is imaged onto a pixel. Applied before or after the computation of brightness as a function of maximum input pixel value, pixel value windowing can be used to suppress uninteresting detail, substantially in the same way as when windowing is applied merely before display rather than before the processing according to FIG. 3.

In one embodiment, the same pixel value windowing operation is applied before computation of each of brightness, saturation and optionally hue according to the process of FIG. 3. However, in another embodiment mutually independent forms of pixel value windowing may be applied before the computation of any one of these properties. Thus for example, different lower bounds may be used before the computation of brightness and before the computation of saturation, the lower bound for the computation of saturation.

Preferably the system has an input for selecting the range that is used for pixel value windowing, or a plurality of ranges that are used for different forms of pixel value windowing before the computation of brightness, saturations and optionally hue respectively. A conventional computer interface may be used as input for the selection of the ranges for example, or a rotating knob or knobs may be used. A user input for this purpose provides the user with an effective control to optimize the image forming process. Alternatively, in some applications, a default selection may be used, in an X-ray system for example a selection that defines a range of pixel values corresponding to an absorption value below that of water to an absorption value above a typical minimum absorption value of bone.

Although a form of pixel value windowing has been described wherein pixel values that are below a selected range of pixel values are replaced by the lower bound of the range and pixel values that are above the range are replaced by the upper bound of the range, it should be understood that other forms of pixel value windowing may be used, for example computation of the pixel values as a smooth saturating function of the input values, that is, as a function that more gradually approaches the lower bound or the upper bound when the input value is above or below the selected range e.g. as a hyperbolic tangent function of the input value, the lower and/or upper bound being less extreme than extrapolations from a linear behaviour in the selected range. As used herein, such smooth saturation is encompassed in the term "pixel-value windowing".

Also, of course, the windowing operation may offset and scale the pixel values prior to the computations of fifth step 25. The pixel values may be scaled to a range of output values from zero to one for example, in proportion to the position of the input values in the pixel-value window range and to zero and one if the input values are below or above the pixel value window range respectively.

It should be appreciated that the process described by means of the flow-chart of FIG. 2 is merely one example of a possible way of using the capacity of color images to combine different source images taken during a respiratory cycle. For example, it should be appreciated that the roles of the maximum and minimum could be interchanged for the determination of brightness. Preferably, when increasing image values in a source image indicate the increased likelihood of the presence of a predetermined type of tissue (e.g. bone) the process is used as described, so that the maximum controls brightness. Conversely when decreasing image values indicate such an increased likelihood the minimum is preferably used to control brightness. In this way presence of the predetermined type of tissue at any of the time points at the pixel location controls the composite image brightness.

In an alternative embodiment this role of maxima and minima may be reversed. If so, the absence of the predetermined type of tissue is determinative for the brightness. This may have use in certain circumstances.

It should be appreciated that instead of the overall maxima and minima values may be used that have a rank near the rank of the maximum or minimum on a sorted list of image values at a pixel position under processing in the different source images. For example, the second or third highest image value may be used instead of the maximum and the second or third lowest image value may be used instead of the minimum. This may be used for example to reduce the effect of noise if sufficient source images are available.

As another example, image processing computer 12 may be arranged to compute the standard deviation or other measure of the spread in the image values at a pixel position under processing in the different source image and the computed value may be used to control saturation. This achieves a similar effect as when the difference between the maximum and minimum is used for this purpose.

Furthermore, the control of brightness has been described so that grey values result at pixel positions where no differences between image values from the source images occur. This is because saturation is used controlled by the spread. Also, although an embodiment has been shown wherein hue is selected independent of spread, it should be understood that in other embodiments both hue and saturation may be controlled by the spread. In this case, line 30 will be curved. In this case hue may be additionally controlled dependent on other properties of the source images, such as the central value.

When an X-ray CT image acquisition device is used the images in the series of source images may be images of a same body slice at different time points. However, instead projection images may be used that combine different slices for a same time point. In a further embodiment the series of source images may even contain images of different slices at the same time point. In this case the composite image uses color to combine depth information. Furthermore, as mentioned, although the invention has been described for a 4D X-ray CT scanner, it should be appreciated that other image acquisition devices may be used. For example, other types of X-ray imaging, NMR imaging, fluoroscopy, acoustical echography etc. may be used. In each case, the invention may be applied to a series of images of the same object (or collection of objects), where the images have been obtained at successive time points in order to detect motion. But in other embodiments different images of different slices of an object at the same time point may be used, or images of the same object at different temperatures or any other physical conditions may be used.

Furthermore, although the invention is primarily directed at radiotherapeutic applications, it should be appreciated that the invention may be applied in other fields as well. First of all a process similar to that shown in FIG. 2 may be applied to other types of medical imaging, including those using movie loops (cines) to display the images such as, but not limited to, fMRI, MRI flow, respiratory and cardiac gated MRI's, gamma camera and PET. For example, the process may be applied to monitoring and predicting impending ruptures in aneurysms. Use of 4D CT for predicting this condition is described in an article titled "Prediction of impending rupture in aneurysms using 4D-CTA: Histopathological verification of real-time minimally invasive tool in ruptured aneurysms" by Y. Kato, M Hayakawa, H. Sano, M. V. Sunil, S. Imizu, S. Watanabe, M. Abe, T. Kanno, published in Minimally invasive neurosurgery 47 (3) pages 131-135 (June 2004). It is described that vessels that are about to rupture pulse to larger volumes with each heart beat than healthy vessels. By applying the process of FIG. 2 to a series of images of such vessels during heart beats a device can be realized that makes it possible to predict this condition with high reliability.

Another application of the invention is positron emission tomography (PET) imaging. A typical example of the application of PET imaging is given in an article titled "Positron emission tomography in non-Hodgkin's lymphoma: Assessment of chemotherapy with fluorodeoxyglucose", by Romer W, Hanauske A R, Ziegler S, Thodtmann R, Weber W, Fuchs C, Enne W, Herz M, Nerl C, Garbrecht M, Schwaiger M, published in BLOOD 91 (12): 4464-4471 Jun. 15, 1998. This study used PET to monitor radioactive activity of F-18 fluorodeoxyglucose (FDG) after it was injected into patients with non-Hodgkin's lymphoma. The study showed FDG was preferentially taken up by tumors as have several other studies. The study also showed that the combination of FDG and PET might be useful in therapy monitoring.

Also, the rate at which FDG is taken up by tumors was shown to be of interest to the study as it has been in several other studies. The PET images were acquired in 31 different spatial slices during the 60 minutes after the intravenous bolus injection of the FDG. All 31 slice were acquire in 30 different time windows or frames spread over the 60 minute interval. The frames intervals were 12 at 10 seconds each, 6 at 20 seconds each, 5 at 60 seconds each, 4 at 5 minutes each and 3 at 10 minutes each.

The present technique is useful in visualizing the change in radioactive decay of over the PET image frames. Detected emission as a function of position may be instead of the X-ray signal in computer tomography device. The percentage of time and/or preferably the arrival time may be used to control hue for example. If desired, the frames can be divided into smaller time intervals than those mentioned in the preceding.

But applications outside the medical field are also possible. For example, the invention may be applied to video surveillance systems. In this case a video camera is provided that is directed at an area under surveillance (e.g. the interior of a shop, an access area to a protected building etc.). A series of grey-scale images of the area under surveillance is obtained over time (e.g. during several second, minutes or hours, or at the same time-point on a number of successive days). These images are then processed substantially as described by means of the flow chart of FIG. 2, in order to generate a composite image that can be displayed on a surveillance monitor. This is particularly advantageous for surveillance, since it increases the effectiveness of surveillance by reducing the risk that events will be missed by an observer in a control room or by a person who looks at the monitor only incidentally. By applying the technique of the invention, the surveillance system provides for visualization of movement in the context of a static image in a way that does not depend on the number of underlying images. Similarly, the invention could be applied to successive astronomical images of a piece of sky, to detect movement. This reduces the need to analyse individual images.

The invention claimed is:

1. A method of forming an image of an object, the method comprising: acquiring a series of at least three source images of the object with an image acquisition device; generating a composite color image from the source images with an image processing device, and determining, for each particular pixel position in the composite image, an amount of spread in the images values among the source images at positions that correspond to the particular pixel position; controlling a color saturation of a color pixel value for the particular pixel position in the composite image dependent on the amount of spread, so that when the amount of spread is zero the color pixel value corresponds to a grey value and the color pixel value deviates increasingly from the grey value which an increase in the amount of spread; displaying the composite image with pixels having pixel color values determined according to the preceding steps with a display device.

2. A method according to claim 1, comprising determining, for the particular pixel position in the composite image, an extreme value that is indicative of an extreme among the image values in the source images at positions that correspond to the particular pixel position; controlling a brightness of the color pixel value for the particular pixel position under control of the extreme value.

3. A method according to claim 2, comprising controlling the brightness according to the formula B=max wherein B is the brightness at the pixel position and "max" is a maximum of the pixel values in the source images at positions that correspond to the particular pixel position, both brightness B and "max" being normalized to a same scale, saturation being controlled according to the formula S=(max-min)/max wherein S is the saturation on a scale from zero to one and min is a minimum the pixel values in the source images at positions that correspond to the particular pixel position.

4. A method according to claim 1, wherein said source images are temporally distributed images of the object.

5. A method according to claim 4, wherein the object is a patient, the method comprising detecting a physiological cycle of the patient, selecting time points distributed at least over the physiological cycle and obtaining the source images of the patient at said time points respectively.

6. A method according to claim 4, comprising imaging internal tissue of a patient, and treating a region of said tissue by radiotherapy, wherein the region is selected based on the composite image.

7. A method according to claim 1, comprising computing a central value for the image values for the particular pixel position in the source images and controlling a hue of the color of the color pixel value under control of said central value.

8. A method according to claim 1, comprising computing information about a time point of a transition in the image values for the particular pixel position in the source images and controlling a hue of the color of the color pixel value under control of said information about the time point.

9. A method according to claim 2, wherein said acquiring is performed so that changes in a predetermined direction in the image value in the source images indicate that there is increased likelihood that a predetermined type of tissue is observed, said selecting of the extreme value involving selecting an image value that is indicative of a highest likelihood of said type of tissue at the particular pixel position in any one of the source images.

10. A method according to claim 1, comprising pixel value windowing to the image values of the source images prior to the determination of the amount of spread.

11. An imaging apparatus, comprising an image acquisition device; an image processing device coupled to the image acquisition device and arranged to form a composite color image from a series of at least three source images from the image acquisition device, and to determine, for each particular pixel position in the composite image, an amount of spread in the images values among the source images at positions that correspond to the particular pixel position; and to control a color saturation of a color pixel value for the particular pixel position in the composite image dependent on the amount of spread, so that when the amount of spread is zero the color pixel value corresponds to a grey value and the color pixel value deviates increasingly from the grey value which an increase in the amount of spread; an image display device coupled to the image processing device, for displaying the composite image with pixels having pixel color values determined by the image processing device.

12. An imaging apparatus according to claim 11, wherein the image processing device is arranged to determine an extreme value that is indicative of an extreme among the image values in the source images at positions that correspond to the particular pixel position; and to control a brightness of a color pixel value for the particular pixel position under control of the extreme value.

13. An imaging apparatus according to claim 12, wherein the image processing device is arranged to control the brightness according to the formula B=max wherein B is the brightness at the pixel position and "max" is a maximum of the pixel values in the source images at positions that correspond to the particular pixel position, both brightness B and "max" being normalized to a same scale, and to control saturation according to the formula S=(max -min)/max wherein S is the saturation on a scale from zero to one and min is a minimum the pixel values in the source images at positions that correspond to the particular pixel position.

14. An imaging apparatus according to claim 11, wherein the image acquisition device is arranged to acquire the source images at temporally distributed time points.

15. An imaging apparatus according to claim 11, comprising a detector for detecting a physiological cycle of the patient, the image acquisition device being arranged to select the time points so that a combination of the time points spans at least the detected cycle.

16. An imaging apparatus according to claim 11, wherein the image processing device is arranged to compute a central value of the image values for the particular pixel position in the source images and to control a hue of the color pixel value under control of said central value.

17. An imaging apparatus according to claim 11, wherein the image acquisition device is an X-ray CT scanner.

18. An imaging apparatus according to claim 11, wherein the image acquisition device is a PET scanner.

19. An imaging apparatus according to claim 12, wherein said image acquisition device is arranged so that changes in a predetermined direction in the image value in the source images indicate that there is increased likelihood that a predetermined type of tissue is observed, the image processing device being arranged so that said selecting of the extreme value involves selecting an image value that is indicative of a highest likelihood of said type of tissue at the particular pixel position in any one of the source images.

20. An imaging apparatus according to claim 11, wherein the image processing device is arranged to perform comprising pixel value windowing to the image values of the source images prior to the determination of the amount of spread.

21. An imaging apparatus according to claim 11, wherein the image processing device is arranged to compute a central value for the image values for the particular pixel position in the source images and controlling a hue of the color of the color pixel value under control of said central value.

22. An imaging apparatus according to claim 11, wherein the image processing device is arranged to compute information about a time point of a transition for the image values for the particular pixel position in the source images and controlling a hue of the color of the color pixel value under control of said information about the time point.

23. An image processing device, comprising an input for receiving source images from an the image acquisition device and an output supplying a composite image for display to an image display device, wherein the image processing device comprises a computation circuit arranged to receive a series of at least three source images form a composite color image, determine, for each particular pixel position in the color image, an amount of spread in the images values among the source images at positions that correspond to the particular pixel position; control a color saturation of a color pixel value for the particular pixel position in the composite image dependent on the amount of spread, so that when the amount of spread is zero the color pixel value corresponds to a grey value and the color pixel value deviates increasingly from the grey value which an increase in the amount of spread.

24. A computer program product comprising a program of instructions on a computer-readable medium which, when executed by a programmable image processing device causes the image processing device to receive a series of at least three source images of an object; form a composite color image from the source images; determine, for each particular pixel position in the composite color image, an amount of spread among pixel values at positions that correspond to the particular pixel position in the source images; control a color saturation of a color pixel value for the particular pixel position in the composite image dependent on the amount of spread, so that when the amount of spread is zero the color pixel value corresponds to a grey value and the color pixel value deviates increasingly from the grey value which an increase in the amount of spread; display the composite image with pixels having pixel color values determined according to the preceding steps.

25. A method of forming an image of an object, the method comprising:
    acquiring a series source images of the object with an image acquisition device, the series comprising at least three source images of the object at temporally distributed time points;
    generating a composite color image from the source images with an image processing device;
    determining an amount of spread in the images' values in the source images at positions that correspond to the particular pixel position in the composite image;
    computing information about a time point of a transition in the pixel values for the particular pixel position in the source images;
    selecting a color pixel value for the particular pixel position dependent on the amount of spread and said information about the time point, a hue of the color of the color pixel value being controlled by said information about the time point;
    displaying the composite image having pixels having pixel color values determined according to the preceding steps with a display device.

26. An imaging apparatus, comprising:
    an image acquisition device configured to acquire images at temporally distributed time points;

an image processing device coupled to the image acquisition device and arranged to form a composite color image from a series of at least three source images of the source images from the image acquisition device, and to determine, for each particular pixel position in the composite image:
  an amount of spread in the images' values among the source images at positions that correspond to the particular pixel position,
  information about a time point of a transition for the image values for the particular pixel position in the source images, and
  to select a color pixel value for the particular pixel position dependent on the amount of spread and the information about the time point, a hue of the color of the color pixel value being controlled by said information about the time point;
an image display device coupled to the image processing device, for displaying the composite image with pixels having pixel color values determined by the image processing device.

27. A method of forming an image of an object, the method comprising
  acquiring a series of source images of the object, the series comprising at least three source images of the object at temporally distributed time points;
  generating a composite color image from the series of source images;
  selecting a color pixel value for each particular pixel position in the composite image dependent on pixel values of the source images at positions that correspond to the particular pixel position;
  displaying the composite image with pixels having pixel color values determined according to the preceding steps;
  wherein:
  an extreme value indicative of an extreme among the image values in the source images at positions corresponding to the particular pixel position is determined for the particular pixel position in the composite image;
  a brightness of the color pixel value for the particular pixel position is dependent on of the extreme value;
  an amount of spread in the image values in the source images at the position corresponding to the particular pixel position is determined,
  a color pixel with non-zero color saturation is displayed when the particular pixel position has amore than zero spread;
  information about a time point of a transition in the pixel values for the particular pixel position in the source images is computed; and
  a hue of the color of the color pixel value is controlled under control of said information about the time point.

28. A method according to claim 27, wherein said computing information about a time point of a transition in the pixel values comprises determining, for each particular pixel position pixel and for each of a series of time points, a maximum or minimum image value of the pixel from a start of measurement up to the time point.

29. A method according to claim 27, comprising use of an edge detection method to detect a time point where the image value of the pixel as a function of time exhibits an edge.

30. An imaging apparatus, comprising:
  an image acquisition device configured acquire images at temporally distributed time points;
  an image processing device coupled to the image acquisition device and arranged to form a composite color image from a series of the source images from the image acquisition device, the series comprising at least three source images, and to determine, for each particular pixel position in the composite image, a color pixel value dependent on pixel values of the series of source images at positions that correspond to the particular pixel position; wherein the image processing device is arranged to determine an extreme value indicative of an extreme among the image values in the source images at positions corresponding to the particular pixel position; and to control a brightness of a color pixel value for the particular pixel position under control of the extreme value, and wherein the image processing device is configured to determine an amount of spread in the image values among the source images at the positions corresponding to the particular pixel position; to cause the image display device to display a color with non zero color saturation when the particular pixel position has a non zero amount of spread; to compute information about a time point of a transition for the image values for the particular pixel position in the source images; and to control a hue of the color of the color pixel value under control of said information about the time point; and
  an image display device coupled to the image processing device, to display the composite image with pixels having pixel color values determined by the image processing device.

* * * * *